United States Patent
Fukuoka et al.

(10) Patent No.: US 8,071,819 B2
(45) Date of Patent: Dec. 6, 2011

(54) INDUSTRIAL PROCESS FOR PRODUCTION OF HIGH-PURITY DIOL

(75) Inventors: Shinsuke Fukuoka, Tokyo (JP); Hironori Miyaji, Tokyo (JP); Hiroshi Hachiya, Tokyo (JP); Kazuhiko Matsuzaki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 659 days.

(21) Appl. No.: 11/991,292

(22) PCT Filed: Dec. 28, 2006

(86) PCT No.: PCT/JP2006/326228
§ 371 (c)(1),
(2), (4) Date: Oct. 29, 2008

(87) PCT Pub. No.: WO2007/080805
PCT Pub. Date: Jul. 19, 2007

(65) Prior Publication Data
US 2009/0156865 A1     Jun. 18, 2009

(30) Foreign Application Priority Data

Jan. 10, 2006  (JP) ................... 2006-002711

(51) Int. Cl.
C07C 31/18 (2006.01)
B01J 19/00 (2006.01)
B01D 3/00 (2006.01)
(52) U.S. Cl. .................. 568/852; 422/211; 202/152
(58) Field of Classification Search ............... 568/852; 422/211; 202/152
See application file for complete search history.

(56) References Cited

U.S. PATENT DOCUMENTS

| | | | |
|---|---|---|---|
| 5,231,212 | A | 7/1993 | Buysch et al. |
| 5,359,118 | A | 10/1994 | Wagner et al. |
| 5,847,189 | A | 12/1998 | Tojo et al. |
| 6,346,638 | B1 | 2/2002 | Tojo et al. |
| 6,479,689 | B1 | 11/2002 | Tojo et al. |
| 2006/0000703 | A1 | 1/2006 | Mason et al. |

FOREIGN PATENT DOCUMENTS

| | | |
|---|---|---|
| EP | 0530615 A2 | 8/1992 |
| EP | 0569812 A1 | 5/1993 |
| EP | 0889025 A1 | 1/1999 |
| EP | 1086940 A1 | 3/2001 |
| EP | 1174406 A1 | 1/2002 |
| EP | 1426086 A1 | 6/2004 |
| JP | 04-198141 A | 7/1992 |
| JP | 04-230243 A | 8/1992 |
| JP | 5-213830 A | 8/1993 |
| JP | 6-9507 A | 1/1994 |
| JP | 8-170086 A | 7/1996 |
| JP | 09-176061 A | 7/1997 |
| JP | 9-183744 A | 7/1997 |
| JP | 09-194435 A | 7/1997 |
| JP | 2002-308804 A | 10/2002 |
| JP | 2003-119168 A | 4/2003 |
| JP | 2003-300936 A | 10/2003 |
| JP | 2003-342209 A | 12/2003 |
| JP | 2004-131394 A | 4/2004 |
| TW | 359668 | 6/1999 |
| TW | 473467 B | 1/2002 |
| TW | 568898 B | 1/2004 |
| TW | 200732291 A | 9/2007 |
| TW | 200734299 A | 9/2007 |
| WO | WO-97/23445 A1 | 7/1997 |
| WO | WO-99/64382 A1 | 12/1999 |
| WO | WO-00/51954 A1 | 9/2000 |
| WO | WO-03/006418 A1 | 1/2003 |
| WO | WO-2005/123638 A1 | 12/2005 |
| WO | WO-2006/030724 A1 | 3/2006 |

OTHER PUBLICATIONS

Supplementary European Search Report dated Oct. 5, 2009 for European application No. 05843606.2.
Japan Petroleum Institute (ed.), "Sekiyu-kagaku Purosesu" ("Petrochemcial Processes"), pp. 120-125, Kodansha, 2001.

Primary Examiner — Sikarl Witherspoon
(74) Attorney, Agent, or Firm — Birch, Stewart, Kolasch & Birch, LLP

(57) ABSTRACT

The invention provides an apparatus and process for producing high-purity diol by taking cyclic carbonate and aliphatic monohydric alcohol as starting materials, continuously feeding the starting materials into column A, carrying out reactive distillation in column A, continuously withdrawing a low boiling point reaction mixture containing a produced dialkyl carbonate and the aliphatic monohydric alcohol from an upper portion of column A, continuously withdrawing a high boiling point reaction mixture containing a produced diol from a lower portion of column A, continuously feeding the high boiling point reaction mixture into distillation column C, distilling off material having a lower boiling point than that of the diol contained in the high boiling point reaction mixture $A_B$ as a column top component and/or a side cut component so as to obtain a column bottom component, continuously feeding the column bottom component into distillation column E, and obtaining the diol.

29 Claims, 1 Drawing Sheet

INDUSTRIAL PROCESS FOR PRODUCTION OF HIGH-PURITY DIOL

TECHNICAL FIELD

The present invention relates to an industrial process for the production of a high-purity diol in which a cyclic carbonate and an aliphatic monohydric alcohol are continuously fed into a reactive distillation column, and carrying out reactive distillation, and a high boiling point reaction mixture having the diol as a main component thereof is continuously withdrawn from the bottom of the reactive distillation column, material having a lower boiling point than that of the diol is distilled off from the high boiling point reaction mixture using a continuous multi-stage distillation column, and a column bottom component from the continuous multi-stage distillation column is fed into a continuous multi-stage distillation column having a specified structure, and the diol is continuously obtained as a side cut component.

BACKGROUND ART

A reactive distillation process for producing a dialkyl carbonate and a diol through reaction between a cyclic carbonate and an aliphatic monohydric alcohol was first disclosed by the present inventors (see Patent Document 1: Japanese Patent Application Laid-Open No. 4-198141, Patent Document 2: Japanese Patent Application Laid-Open No. 4-230243, Patent Document 3: Japanese Patent Application Laid-Open No. 9-176061, Patent Document 4: Japanese Patent Application Laid-Open No. 9-183744, Patent Document 5: Japanese Patent Application Laid-Open No. 9-194435, Patent Document 6: International Publication No. WO97/23445 (corresponding to European Patent No. 0889025, and U.S. Pat. No. 5,847,189), Patent Document 7: International Publication No. WO99/64382 (corresponding to European Patent No. 1086940, and U.S. Pat. No. 6,346,638), Patent Document 8: International Publication No. WO00/51954 (corresponding to European Patent No. 1174406, and U.S. Pat. No. 6,479,689), Patent Document 9: Japanese Patent Application Laid-Open No. 2002-308804, Patent Document 10: Japanese Patent Application Laid-Open No. 2004-131394), and patent applications in which such a reactive distillation system is used have subsequently also been filed by other companies (see Patent Document 11: Japanese Patent Application Laid-Open No. 5-213830 (corresponding to European Patent No. 0530615, and U.S. Pat. No. 5,231,212), Patent Document 12: Japanese Patent Application Laid-Open No. 6-9507 (corresponding to European Patent No. 0569812, and U.S. Pat. No. 5,359,118), Patent Document 13: Japanese Patent Application Laid-Open No. 2003-119168 (corresponding to International Publication No. WO03/006418), Patent Document 14: Japanese Patent Application Laid-Open No. 2003-300936, Patent Document 15: Japanese Patent Application Laid-Open No. 2003-342209). In the case of using the reactive distillation system for this reaction, the reaction can be made to proceed with a high conversion. However, reactive distillation processes proposed hitherto have related to producing the dialkyl carbonate and the diol either in small amounts or for a short period of time, and have not related to carrying out the production on an industrial scale stably for a prolonged period of time. That is, these processes have not attained the object of producing a diol continuously in a large amount (e.g. not less than 1 ton/hr) stably for a prolonged period of time (e.g. not less than 1000 hours, preferably not less than 3000 hours, more preferably not less than 5000 hours).

For example, the maximum values of the height (H: cm), diameter (D: cm), and number of stages (n) of the reactive distillation column, the amount produced P (kg/hr) of ethylene glycol, and the continuous production time T (hr) in examples disclosed for the production of dimethyl carbonate (DMC) and ethylene glycol (EG) from ethylene carbonate and methanol are as in Table 1.

TABLE 1

| PATENT DOCUMENT | H: cm | D: cm | NO. STAGES: n | P: kg/hr | T: hr |
|---|---|---|---|---|---|
| 1 | 100 | 2 | 30 | 0.073 | 400 |
| 4 | 160 | 5 | 40 | 0.213 | NOTE 5 |
| 5 | 160 | 5 | 40 | 0.358 | NOTE 5 |
| 7 | 200 | 4 | PACKING COLUMN (Dixon) | 0.528 | NOTE 5 |
| 8 | NOTE 1 | 5 | 60 | 0.140 | NOTE 5 |
| 9 | NOTE 1 | 5 | 60 | 0.161 | NOTE 5 |
| 10 | NOTE 1 | 5 | 60 | 0.161 | NOTE 5 |
| 11 | 250 | 3 | PACKING COLUMN (Raschig) | 0.154 | NOTE 5 |
| 12 | NOTE 2 | NOTE 2 | NOTE 2 | 0.256 | NOTE 5 |
| 13 | NOTE 3 | NOTE 3 | 42 | NOTE 4 | NOTE 5 |
| 14 | NOTE 3 | NOTE 3 | 30 | 2490 | NOTE 5 |
| 15 | 200 | 15 | PACKING COLUMN (BX) | 19 | NOTE 5 |

NOTE 1: OLDERSHAW DISTILLATION COLUMN.
NOTE 2: NO DESCRIPTION WHATSOEVER DEFINING DISTILLATION COLUMN.
NOTE 3: ONLY DESCRIPTION DEFINING DISTILLATION COLUMN IS NUMBER OF STAGES.
NOTE 4: NO DESCRIPTION WHATSOEVER OF PRODUCED AMOUNT.
NOTE 5: NO DESCRIPTION WHATSOEVER REGARDING STABLE PRODUCTION FOR PROLONGED PERIOD OF TIME.

In Patent Document 14 (Japanese Patent Application Laid-Open No. 2003-300936), it is stated at paragraph 0060 that "The present example uses the same process flow as for the preferred mode shown in FIG. 1 described above, and was carried out with the object of operating a commercial scale apparatus for producing dimethyl carbonate and ethylene glycol through transesterification by a catalytic conversion reaction between ethylene carbonate and methanol. Note that the following numerical values in the present example can be adequately used in the operation of an actual apparatus", and as that example it is stated that 3750 kg/hr of dimethyl carbonate and 2490 kg/hr of ethylene glycol were specifically produced. The scale described in that example corresponds to an annual production of 30,000 or more tons of dimethyl carbonate, and hence this implies that operation of the world's largest scale commercial plant using this process had been carried out at the time of the filing of the patent application for Patent Document 14 (Japanese Patent Application Laid-Open No. 2003-300936) (Apr. 9, 2002). However, even at the time of filing the present application, there is not the above fact at all. Moreover, in the example of Patent Document 14 (Japanese Patent Application Laid-Open No. 2003-300936), exactly the same value as the theoretically calculated value is stated for the amount of dimethyl carbonate produced, but the yield for ethylene glycol is approximately 85.6%, and the selectivity is approximately 88.4%, and hence it cannot really be said that a high yield and high selectivity have been attained. In particular, the low selectivity indicates that this process has a fatal drawback as an industrial production process. (Note also that Patent Document 14 (Japanese Patent Application Laid-Open No. 2003-300936) was deemed to have been withdrawn on Jul. 26, 2005 due to examination not having been requested).

With such a reactive distillation process, there are very many causes of fluctuation such as composition variation due to reaction and composition variation due to distillation in the distillation column, and temperature variation and pressure variation in the column, and hence continuing stable operation for a prolonged period of time is often accompanied by difficulties, and in particular these difficulties are further increased in the case of handling large amounts. To continue mass production of a dialkyl carbonate and a diol using the reactive distillation process stably for a prolonged period of time while maintaining high yield and high selectivity, and thus produce a high-purity diol, the process must be cleverly devised. However, the only description of continuous stable production for the prolonged period of time with the reactive distillation process proposed hitherto has been the 200 to 400 hours in Patent Document 1 (Japanese Patent Application Laid-Open No. 4-198141) and Patent Document 2 (Japanese Patent Application Laid-Open No. 4-230243).

The present inventors have proposed an industrial reactive distillation process that enables a dialkyl carbonate and a diol to be mass-produced continuously and stably for a prolonged period of time with high yield and high selectivity, but in addition to this, a process enabling a high-purity diol to be separated out and purified in a large amount stably for a prolonged period of time from a high boiling point reaction mixture continuously withdrawn in a large amount from a lower portion of the reactive distillation column is also required, a process for producing a large amount of a high-purity diol with a high yield having been called for. The present invention has been devised to attain this object.

As shown in Table 1, with the exception of Patent Document 14 (Japanese Patent Application Laid-Open No. 2003-300936), the amount of the diol produced per hour using the reactive distillation processes proposed hitherto has been a small amount. Moreover, with the process of Patent Document 14 (Japanese Patent Application Laid-Open No. 2003-300936), it is stated that approximately 2490 kg/hr of ethylene glycol containing approximately 130 kg/hr of unreacted ethylene carbonate and approximately 226 kg/hr of dihydroxyethyl carbonate was obtained as a column bottom component from a fourth step distillation column. However, this is merely a statement of the composition of the reaction mixture, there being no description whatsoever of production of a high-purity diol.

As a process for producing a diol of relatively high purity using reactive distillation and a diol purifying column, a process is known in which the diol is obtained from a side cut of the diol purifying column. For example, in the example (FIG. 5) in Patent Document 12 (Japanese Patent Application Laid-Open No. 6-9507 (corresponding to European Patent No. 0569812, and U.S. Pat. No. 5,359,118)), a high boiling point reaction mixture withdrawn from a lower portion of a reactive distillation column is fed into a thin film evaporator (III), high boiling point matter obtained therefrom is fed into a thin film evaporator (IV), low boiling point evaporated matter obtained therefrom is fed into a distillation column (VII), and ethylene glycol is obtained as a side cut component 22 from an enrichment section of the distillation column (VII), and then purification is further carried out using a purifier (IX), whereby high-purity ethylene glycol is produced in an amount of 255 g/hr. That is, in the process of Patent Document 12 (Japanese Patent Application Laid-Open No. 6-9507 (corresponding to European Patent No. 0569812, and U.S. Pat. No. 5,359,118)), high-purity ethylene glycol is not obtained from the high boiling point reaction mixture until four purifying apparatuses have been used. Furthermore, the process of Patent Document 12 (Japanese Patent Application Laid-Open No. 6-9507 (corresponding to European Patent No. 0569812, and U.S. Pat. No. 5,359,118)) is a process in which a small amount of ethylene glycol is produced, there being no suggestions whatsoever regarding a process for producing a large amount (e.g. not less than 1 ton/hr) of a diol stably for a prolonged period of time (e.g. not less than 5000 hours).

Moreover, in, for example, example 1 (FIG. 5) in Patent Document 15 (Japanese Patent Application Laid-Open No. 2003-342209), a high boiling point reaction mixture withdrawn from a lower portion of a reactive distillation column is fed into a second distillation column 4, high boiling point matter obtained therefrom is fed into a hydrolysis reactor 7, the reaction mixture therefrom is fed into a decarboxylation tank (gas-liquid separator 8), a liquid component obtained therefrom is fed into a third distillation column 10, and ethylene glycol is produced in an amount of 19 kg/hr as a side cut component from a stripping section of the third distillation column 10. However, with the process of Patent Document 15 (Japanese Patent Application Laid-Open No. 2003-342209), the ethylene glycol obtained contains 0.2% by weight of diethylene glycol. To obtain ethylene glycol of a high purity as required as a starting material for a PET fiber or a PET resin using the process of Patent Document 15 (Japanese Patent Application Laid-Open No. 2003-342209), at least one further purifying apparatus is thus required. That is, with the process of Patent Document 15 (Japanese Patent Application Laid-Open No. 2003-342209), ethylene glycol is obtained from a side cut outlet installed in the stripping section, which is below an inlet for feeding into the distillation column, but the purity of the ethylene glycol is insufficient, and moreover the process of Patent Document 15 (Japanese Patent Application Laid-Open No. 2003-342209) is a process in which a small amount of ethylene glycol is produced, there being no suggestions whatsoever regarding a process for producing a large amount (e.g. not less than 1 ton/hr) of a diol stably for a prolonged period of time (e.g. not less than 5000 hours).

Moreover, in, for example, example 10 (FIG. 6) in Patent Document 8 (International Publication No. WO00/51954 (corresponding to European Patent No. 1174406, and U.S. Pat. No. 6,479,689)) and example 1 (FIG. 1) in Patent Document 9 (Japanese Patent Application Laid-Open No. 2002-308804), high-purity ethylene glycol is obtained from a side cut outlet installed in an enrichment section of an EG purifying column 41, which is above an inlet for feeding into the column, but in each case the amount produced is a small amount of less than 200 g/hr, there being no suggestions whatsoever regarding a process for producing a large amount (e.g. not less than 1 ton/hr) of a diol stably for a prolonged period of time (e.g. not less than 5000 hours).

Approximately 16 million tons per year (2004) of ethylene glycol is produced worldwide, but hitherto all of this has been through a hydration method in which water is added to ethylene oxide. However, as shown by the statement "Production of EG (ethylene glycol) is by a hydration reaction of EO (ethylene oxide), the reaction generally being carried out . . . at 150 to 200° C. At this time, not only is the target substance MEG (monoethylene glycol) produced, but moreover DEG (diethylene glycol) and TEG (triethylene glycol) are also by-produced. The proportions of these products depend on the water/EO ratio, and to obtain MEG with a selectivity of approximately 90%, the water/EO ratio must be made to be approximately 20 as a molar ratio. A large amount of water must thus be distilled off in an EG purification step, and a large amount of thermal energy is consumed in this. . . . With regard to synthesis of EG from EO, it is not an overstatement to say that this is an imperfect process from the viewpoint of energy efficiency." in Non-Patent Document 1 (Japan Petroleum Institute (ed.), "Sekiyu-kagaku Purosesu" ("Petrochemical Processes"), pages 120 to 125, Kodansha, 2001), this industrial production process (conventional process) has great drawbacks both from the perspective of the ethylene glycol yield and selectivity, and the perspective of energy saving.

DISCLOSURE OF INVENTION

Problems to be Solved by the Invention

It is an object of the present invention to provide a specific apparatus and process for producing a high-purity diol by taking a cyclic carbonate and an aliphatic monohydric alcohol as starting materials, continuously feeding the starting materials into a continuous multi-stage distillation column A in which a catalyst is present, carrying out reactive distillation in the column A, continuously withdrawing a low boiling point reaction mixture $A_T$ containing a produced dialkyl carbonate and the aliphatic monohydric alcohol from an upper portion of the column A in a gaseous form, continuously withdrawing a high boiling point reaction mixture $A_B$ containing a produced diol from a lower portion of the column A in a liquid form, continuously feeding the high boiling point reaction mixture $A_B$ into a continuous multi-stage distillation column C, distilling off material having a lower boiling point than the diol contained in the high boiling point reaction mixture $A_B$ as a column top component $C_T$ and/or a side cut component $C_S$ so as to obtain a column bottom component $C_B$, continuously feeding the column bottom component $C_B$ into a continuous multi-stage distillation column E, and obtaining the diol as a side cut component $E_S$ from a side cut outlet of the continuous multi-stage distillation column E. Moreover, it is an object to thus provide a specific industrial apparatus and industrial production process that are inexpensive and, for example, enable the high-purity diol to be produced in an amount of not less than 1 ton/hr stably for a prolonged period of time (e.g. not less than 1000 hours, preferably not less than 3000 hours, more preferably not less than 5000 hours).

That is, in a first aspect of the present invention, there are provided:

1. an industrial process for the production of a high-purity diol in which a high-purity diol is produced by taking a cyclic carbonate and an aliphatic monohydric alcohol as starting materials, continuously feeding the starting materials into a continuous multi-stage distillation column A in which a catalyst is present, carrying out reactive distillation in said column A, continuously withdrawing a low boiling point reaction mixture $A_T$ containing a produced dialkyl carbonate and the aliphatic monohydric alcohol from an upper portion of the column A in a gaseous form, continuously withdrawing a high boiling point reaction mixture $A_B$ containing a produced diol from a lower portion of the column A in a liquid form, continuously feeding said high boiling point reaction mixture $A_B$ into a continuous multi-stage distillation column C, distilling off material having a lower boiling point than the diol contained in said high boiling point reaction mixture $A_B$ as a column top component $C_T$ and/or a side cut component $C_S$ so as to obtain a column bottom component $C_B$, continuously feeding the column bottom component $C_B$ into a continuous multi-stage distillation column E, and obtaining the diol as a side cut component $E_S$ from a side cut outlet of the continuous multi-stage distillation column E, wherein:

(a) said continuous multi-stage distillation column E comprises a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (9):

$$400 \leq L_1 \leq 3000 \quad (1)$$

$$50 \leq D_1 \leq 700 \quad (2)$$

$$2 \leq L_1/D_1 \leq 50 \quad (3)$$

$$3 \leq n_1 \leq 30 \quad (4)$$

$$600 \leq L_2 \leq 4000 \quad (5)$$

$$100 \leq D_2 \leq 1000 \quad (6)$$

$$2 \leq L_2/D_2 \leq 30 \quad (7)$$

$$5 \leq n_2 \leq 50 \quad (8) \text{ and}$$

$$D_1 \leq D_2 \quad (9);$$

(b) the enrichment section of said continuous multi-stage distillation column E has at least one chimney tray as an internal installed therein, said chimney tray having installed therein at least two chimneys each having an opening having a cross-sectional area S (cm$^2$) satisfying the formula (10):

$$50 \leq S \leq 2000 \quad (10),$$

and each of the chimneys being such that a height h (cm) from the opening of the chimney to a gas outlet of the chimney satisfies the formula (11):

$$20 \leq h \leq 100 \quad (11); \text{ and}$$

(c) the diol is continuously withdrawn in a liquid form from the side cut outlet, which is connected to a liquid collecting section of said chimney tray of said continuous multi-stage distillation column E, 2. the process according to item 1, wherein a produced amount of the high-purity diol is not less than 1 ton/hr,
3. the process according to item 1 or 2, wherein $L_1$, $D_1$, $L_1/D_1$, $n_1$, $L_2$, $D_2$, $L_2/D_2$, and $n_2$ for said continuous multi-stage distillation column E satisfy $500 \leq L_1 \leq 2000$, $100 \leq D_1 \leq 500$, $3 \leq L_1/D_1 \leq 20$, $5 \leq n_1 \leq 20$, $700 \leq L_2 \leq 3000$, $120 \leq D_2 \leq 800$, $3 \leq L_2/D_2 \leq 20$, $7 \leq n_2 \leq 30$, and $D_1 < D_2$,
4. the process according to any one of items 1 to 3, wherein an internal excluding the chimney tray in each of the stripping section and the enrichment section of said continuous multi-stage distillation column E is a tray and/or a packing, 5. the process according to item 4, wherein the internal excluding the chimney tray in each of the stripping section and the enrichment section of said continuous multi-stage distillation column E is the tray,
6. the process according to item 5, wherein said tray is a sieve tray,
7. the process according to item 6, wherein said sieve tray has 150 to 1200 holes/m$^2$ in a sieve portion thereof, and a cross-sectional area per hole in a range of from 0.5 to 5 cm$^2$,
8. the process according to item 6 or 7, wherein said sieve tray has 200 to 1100 holes/m$^2$ in a sieve portion thereof, and a cross-sectional area per hole in a range of from 0.7 to 4 cm$^2$,
9. the process according to any one of items 6 to 8, wherein said sieve tray has 250 to 1000 holes/m$^2$ in a sieve portion thereof, and a cross-sectional area per hole in a range of from 0.9 to 3 cm$^2$,
10. the process according to any one of items 6 to 9, wherein an aperture ratio (a ratio of a total cross-sectional area of the hole in one tray stage to an area of the tray) of said sieve tray in the stripping section of said continuous multi-stage distillation column E is in a range of from 3 to 25%,
11. the process according to any one of items 6 to 10, wherein an aperture ratio (a ratio of a total cross-sectional area of the hole in one tray stage to an area of the tray) of said sieve trays in the enrichment of said continuous multi-stage distillation column E is in a range of from 2 to 20%,
12. the process according to any one of items 1 to 11, wherein an aperture ratio (a ratio of a total cross-sectional area of the opening in the chimney to an area of the chimney tray including the total cross-sectional area of the opening) of the chimney tray is in a range of from 5 to 40%,
13. the process according to any one of items 1 to 12, wherein a column bottom temperature of said continuous multi-stage distillation column E is in a range of from 110 to 210° C.,
14. the process according to any one of items 1 to 13, wherein a reflux ratio of said continuous multi-stage distillation column E is in a range of from 6 to 100,
15. the process according to any one of items 1 to 14, wherein a purity of the diol in said side cut component $E_S$ is not less than 99%,
16. the process according to any one of items 1 to 15, wherein a purity of the diol in said side cut component $E_S$ is not less than 99.9%.

Further, according to the second aspect of the present invention, there are provided:

17. a high-purity diol produced by the process according to any one of items 1 to 16, which comprises a content of high boiling point impurities such as a dialkylene glycol of not more than 200 ppm, and a halogen content of not more than 0.1 ppm,
18. a high-purity diol produced by the process according to any one of claims 1 to 16, which comprises a content of high boiling point impurities such as a dialkylene glycol of not more than 100 ppm, and a halogen content of not more than 1 ppb.

Furthermore, according to the third aspect of the present invention, there are provided:

19. a continuous multi-stage distillation column being a continuous multi-stage distillation column E for producing a high-purity diol by taking a cyclic carbonate and an aliphatic monohydric alcohol as starting materials, continuously feeding the starting materials into a continuous multi-stage distillation column A in which a catalyst is present, carrying out reactive distillation in said column A, continuously withdrawing a low boiling point reaction mixture $A_T$ containing a produced dialkyl carbonate and the aliphatic monohydric alcohol from an upper portion of said column A in a gaseous form, continuously withdrawing a high boiling point reaction mixture $A_B$ containing a produced diol from a lower portion of said column A in a liquid form, continuously feeding said high boiling point reaction mixture $A_B$ into the continuous multi-stage distillation column C, distilling off material having a lower boiling point than the diol contained in said high boiling point reaction mixture $A_B$ as a column top component $C_T$ and/or a side cut component $C_S$ so as to obtain a column bottom component $C_B$, continuously feeding the column bottom component $C_B$ into said continuous multi-stage distillation column E, and obtaining the diol as a side cut component $E_S$ from a side cut outlet of the continuous multi-stage distillation column E, wherein:

(a) said continuous multi-stage distillation column E comprises a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (9):

$$400 \leq L_1 \leq 3000 \quad (1)$$

$$50 \leq D_1 \leq 700 \quad (2)$$

$$2 \leq L_1/D_1 \leq 50 \quad (3)$$

$$3 \leq n_1 \leq 30 \quad (4)$$

$$600 \leq L_2 \leq 4000 \quad (5)$$

$$100 \leq D_2 \leq 1000 \quad (6)$$

$$2 \leq L_2/D_2 \leq 30 \quad (7)$$

$$5 \leq n_2 \leq 50 \quad (8) \text{ and}$$

$$D_1 \leq D_2 \quad (9);$$

(b) the enrichment section of said continuous multi-stage distillation column E has at least one chimney tray as an internal installed therein, said chimney tray having installed therein at least two chimneys each having an opening having a cross-sectional area S (cm$^2$) satisfying the formula (10):

$$50 \leq S \leq 2000 \quad (10),$$

and each of the chimneys being such that a height h (cm) from the opening of the chimney to a gas outlet of the chimney satisfies the formula (II):

$$20 \leq h \leq 100 \quad (11); \text{ and}$$

(c) the side cut outlet installed for continuously withdrawing the high-purity diol in a liquid form from said continuous multi-stage distillation column E is connected to a liquid collecting section of said chimney tray, 20. the continuous multi-stage distillation column according to item 19, wherein $L_1$, $D_1$, $L_1/D_1$, $n_1$, $L_2$, $D_2$, $L_2/D_2$, and $n_2$ satisfy $500 \leq L_1 \leq 2000$, $100 \leq D_1 \leq 500$, $3 \leq L_1/D_1 \leq 20$, $5 \leq n_1 \leq 20$, $700 \leq L_2 \leq 3000$, $120 \leq D_2 \leq 800$, $3 \leq L_2/D_2 \leq 20$, $7 \leq n_2 \leq 30$, and $D_1 < D_2$,
21. the continuous multi-stage distillation column according to item 19 or 20, wherein an internal excluding the chimney tray in each of the stripping section and the enrichment section is a tray and/or a packing, 22. the continuous multi-stage distillation column according to item 21, wherein the internal excluding the chimney tray in each of the stripping section and the enrichment section is the tray,
23. the continuous multi-stage distillation column according to item 22, wherein said tray is a sieve tray,
24. the continuous multi-stage distillation column according to item 23, wherein said sieve trays has 150 to 1200 holes/m$^2$ in a sieve portion thereof, and a cross-sectional area per hole in a range of from 0.5 to 5 cm$^2$,
25. the continuous multi-stage distillation column according to item 23 or 24, wherein said sieve trays has 200 to 1100 holes/m$^2$ in a sieve portion thereof, and a cross-sectional area per hole in a range of from 0.7 to 4 cm$^2$,
26. the continuous multi-stage distillation column according to any one of items 23 to 25, wherein said sieve trays has 250 to 1000 holes/m$^2$ in a sieve portion thereof, and a cross-sectional area per hole in a range of from 0.9 to 3 cm$^2$,
27. the continuous multi-stage distillation column according to any one of items 23 to 26, wherein an aperture ratio (a ratio of a total cross-sectional area of the hole in one tray stage to an area of the tray) of said sieve tray in the stripping section is in a range of from 3 to 25%,
28. the continuous multi-stage distillation column according to any one of items 23 to 27, wherein an aperture ratio (a ratio of a total cross-sectional area of the hole in one tray stage to an area of the tray) of said sieve tray in the enrichment section is in a range of from 2 to 20%,
29. the continuous multi-stage distillation column according to any one of items 23 to 28, wherein an aperture ratio (a ratio of a total cross-sectional area of the opening in the chimney to an area of the chimney tray including the total cross-sectional area of the opening) of the chimney tray is in a range of from 5 to 40%.

ADVANTAGEOUS EFFECTS OF THE INVENTION

It has been found that according to the specific apparatus and process provided by the present invention, a high-purity diol can be produced from a cyclic carbonate and an aliphatic monohydric alcohol stably for a prolonged period of time on an industrial scale with a high yield (e.g. generally not less than 97%, preferably not less than 98%, more preferably not less than 99%, based on the cyclic carbonate used). That is, according to the present invention, there can be provided an industrial apparatus and industrial production process that are inexpensive and, for example, enable a high-purity diol of purity not less than 99.9% as required as a starting material for a PET fiber or a PET resin to be produced in an amount of not less than 1 ton/hr stably for a prolonged period of time (e.g. not less than 1000 hours, preferably not less than 3000 hours, more preferably not less than 5000 hours).

Moreover, the process according to the present invention differs from the conventional ethylene glycol production process in that high-purity ethylene glycol can be produced by the process according to the present invention with a high yield and a high selectivity without using a large amount of water, and thus achieves excellent effects as an industrial production process that simultaneously solves two long-standing problems with the conventional industrial production process (low selectivity, high energy use).

DESCRIPTION OF REFERENCE NUMERALS

Figure 1:
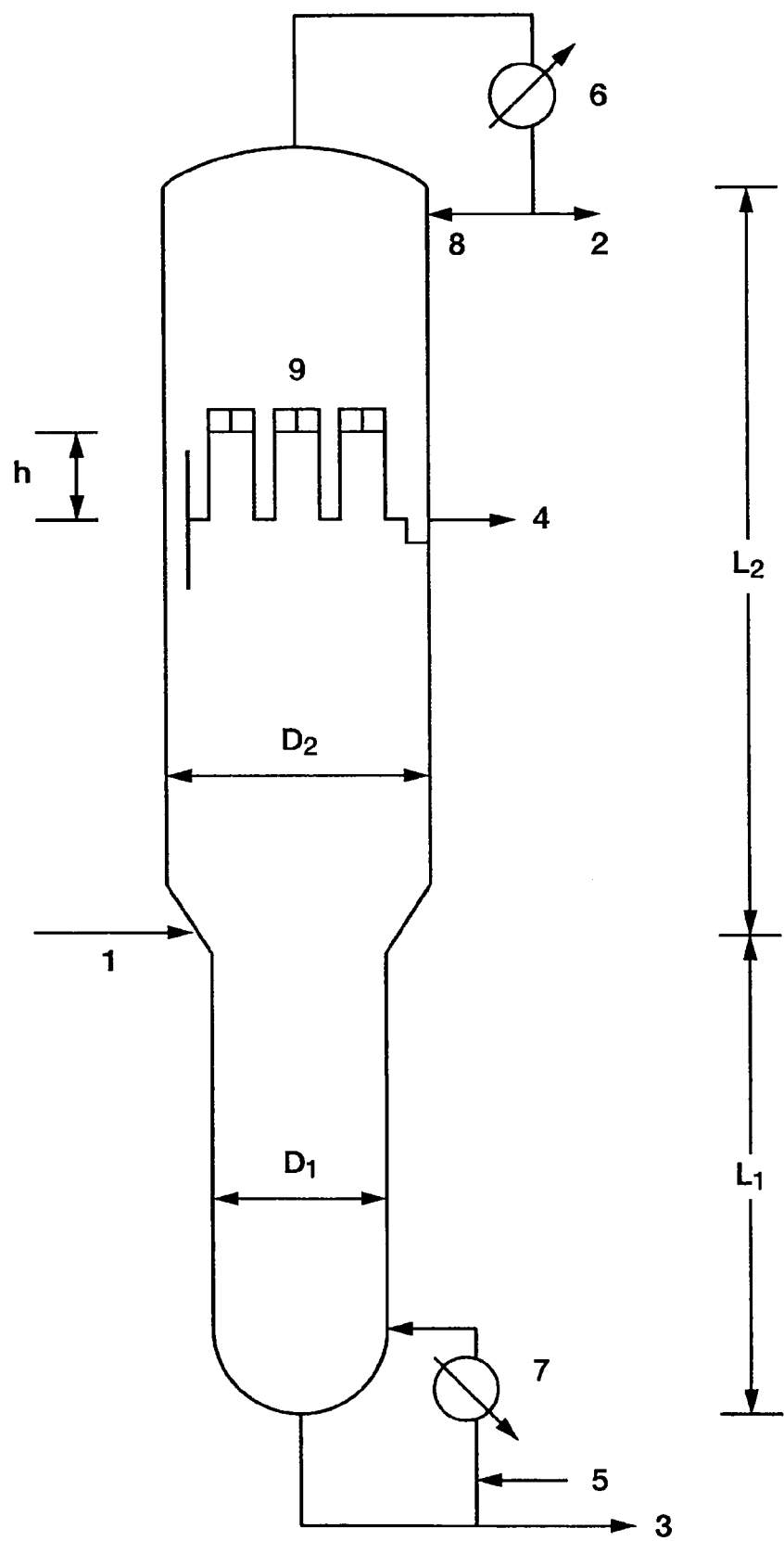
FIG. 1 is a schematic view showing an example of a continuous multi-stage distillation column E preferable for carrying out the present invention, n$_1$ and n$_2$ stages of trays being installed in a stripping section and an enrichment section respectively as an internal in a trunk portion, and one chimney tray stage being installed in the enrichment section above an inlet 1 (in FIG. 1, the trays except for the chimney tray are omitted).

1: inlet, 2: outlet of column top component $E_T$, 3: outlet of column bottom component $E_B$, 4: outlet of side cut component $E_S$, 5: inlet, 6: heat exchanger, 7: reboiler, 8: inlet of reflux liquid, 9: chimney tray, h: height (cm) from an opening of chimney to a gas outlet of chimney, $L_1$: length (cm) of stripping section of continuous multi-stage distillation column E, $L_2$: length of enrichment section of continuous multi-stage distillation column E, $D_1$: inside diameter (cm) of stripping section of continuous multi-stage distillation column E, $D_2$: inside diameter (cm) of enrichment section of continuous multi-stage distillation column E.

BEST MODE FOR CARRYING OUT THE INVENTION

Following is a detailed description of the present invention.

The reaction of the present invention is a reversible equilibrium transesterification reaction represented by the following formula in which a dialkyl carbonate and a diol are produced from a cyclic carbonate and an aliphatic monohydric alcohol;

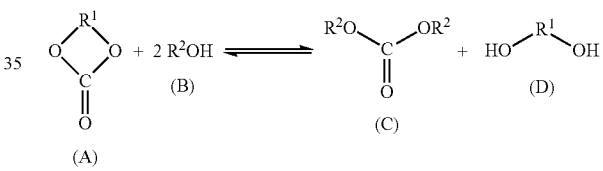

wherein R$^1$ represents a bivalent group —(CH$_2$)$_m$— (m is an integer from 2 to 6), one or more of the hydrogens thereof being optionally substituted with an alkyl group or aryl group having 1 to 10 carbon atoms. Moreover, R$^2$ represents a monovalent aliphatic group having 1 to 12 carbon atoms, one or more of the hydrogens thereof being optionally substituted with an alkyl group or aryl group having 1 to 10 carbon atoms.

The cyclic carbonate used as a starting material in the present invention is a compound represented by (A) in the above formula. For example, an alkylene carbonate such as ethylene carbonate or propylene carbonate, or 1,3-dioxacyclohexa-2-one, 1,3-dioxacyclohepta-2-one, or the like can be preferably used, ethylene carbonate or propylene carbonate being more preferably used due to ease of procurement and so on, and ethylene carbonate being particularly preferably used.

Moreover, the aliphatic monohydric alcohol used as the other starting material is a compound represented by (B) in the above formula, one having a lower boiling point than that of the diol produced being used. Although possibly varying depending on the type of the cyclic carbonate used, examples of aliphatic monohydric alcohol include methanol, ethanol, propanol (isomers), allyl alcohol, butanol (isomers), 3-buten-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers), and so on. Furthermore, these aliphatic monohydric alcohols may be substituted with substituents such as halogens, lower alkoxy groups, cyano groups, alkoxycarbonyl groups, aryloxycarbonyl groups, acyloxy groups, and nitro groups.

Of such aliphatic monohydric alcohols, ones preferably used are alcohols having 1 to 6 carbon atoms, more preferably alcohols having 1 to 4 carbon atoms, i.e. methanol, ethanol, propanol (isomers), and butanol (isomers). In the case of using ethylene carbonate or propylene carbonate as the cyclic carbonate, preferable aliphatic monohydric alcohols are methanol and ethanol, methanol being particularly preferable.

In the process of the present invention, a catalyst is made to be present in a reactive distillation column A. The method of making the catalyst be present in the reactive distillation column A may be any method, but in the case, for example, of a homogeneous catalyst that dissolves in the reaction liquid under the reaction conditions, the catalyst can be made to be present in a liquid phase in the reactive distillation column by feeding the catalyst into the reactive distillation column continuously, or in the case of a heterogeneous catalyst that does not dissolve in the reaction liquid under the reaction conditions, the catalyst can be made to be present in the reaction system by disposing the catalyst as a solid in the reactive distillation column; these methods may also be used in combination.

In the case that a homogeneous catalyst is continuously fed into the reactive distillation column, the homogeneous catalyst may be fed in together with the cyclic carbonate and/or the aliphatic monohydric alcohol, or may be fed in at a different position to the starting materials. The reaction actually proceeds in the distillation column in a region below the position at which the catalyst is fed in, and hence it is preferable to feed the catalyst into a region between the top of the column and the position(s) at which the starting materials are fed in. The catalyst must be present in at least 5 stages, preferably at least 7 stages, more preferably at least 10 stages.

Moreover, in the case of using a heterogeneous solid catalyst, the catalyst must be present in at least 5 stages, preferably at least 7 stages, more preferably at least 10 stages. A solid catalyst that also has an effect as a packing in the distillation column may also be used.

As the catalyst used in the present invention, any of various catalysts known from hitherto can be used. Examples include;

alkali metals and alkaline earth metals such as lithium, sodium, potassium, rubidium, cesium, magnesium, calcium, strontium, and barium;

basic compounds of alkali metals and alkaline earth metals such as hydrides, hydroxides, alkoxides, aryloxides, and amides;

basic compounds of alkali metals and alkaline earth metals such as carbonates, bicarbonates, and organic acid salts;

tertiary amines such as triethylamine, tributylamine, trihexylamine, and benzyldiethylamine;

nitrogen-containing heteroaromatic compounds such as N-alkylpyrroles, N-alkylindoles, oxazoles, N-alkylimidazoles, N-alkylpyrazoles, oxadiazoles, pyridine, alkylpyridines, quinoline, alkylquinolines, isoquinoline, alkylisoquinolines, acridine, alkylacridines, phenanthroline, alkylphenanthrolines, pyrimidine, alkylpyrimidines, pyrazine, alkylpyrazines, triazines, and alkyltriazines;

cyclic amidines such as diazobicycloundecene (DBU) and diazobicyclononene (DBN);

thallium compounds such as thallium oxide, thallium halides, thallium hydroxide, thallium carbonate, thallium nitrate, thallium sulfate, and thallium organic acid salts;

tin compounds such as tributylmethoxytin, tributylethoxytin, dibutyldimethoxytin, diethyldiethoxytin, dibutyldiethoxytin, dibutylphenoxytin, diphenylmethoxytin, dibutyltin acetate, tributyltin chloride, and tin 2-ethylhexanoate;

zinc compounds such as dimethoxyzinc, diethoxyzinc, ethylenedioxyzinc, and dibutoxyzinc;

aluminum compounds such as aluminum trimethoxide, aluminum triisopropoxide, and aluminum tributoxide;

titanium compounds such as tetramethoxytitanium, tetraethoxytitanium, tetrabutoxytitanium, dichlorodimethoxytitanium, tetraisopropoxytitanium, titanium acetate, and titanium acetylacetonate;

phosphorus compounds such as trimethylphosphine, triethylphosphine, tributylphosphine, triphenylphosphine, tributylmethylphosphonium halides, trioctylbutylphosphonium halides, and triphenylmethylphosphonium halides;

zirconium compounds such as zirconium halides, zirconium acetylacetonate, zirconium alkoxides, and zirconium acetate;

lead and lead-containing compounds, for example lead oxides such as $PbO$, $PbO_2$, and $Pb_3O_4$;

lead sulfides such as $PbS$, $Pb_2S_3$, and $PbS_2$;

lead hydroxides such as $Pb(OH)_2$, $Pb_3O_2(OH)_2$, $Pb_2[PbO_2(OH)_2]$, and $Pb_2O(OH)_2$;

plumbites such as $Na_2PbO_2$, $K_2PbO_2$, $NaHPbO_2$, and $KHPbO_2$;

plumbates such as $Na_2PbO_3$, $Na_2H_2PbO_4$, $K_2PbO_3$, $K_2[Pb(OH)_6]$, $K_4PbO_4$, $Ca_2PbO_4$, and $CaPbO_3$;

lead carbonates and basic salts thereof such as $PbCO_3$ and $2PbCO_3 \cdot Pb(OH)_2$;

alkoxylead compounds and aryloxylead compounds such as $Pb(OCH_3)_2$, $(CH_3O)Pb(OPh)$, and $Pb(OPh)_2$;

lead salts of organic acids, and carbonates and basic salts thereof, such as $Pb(OCOCH_3)_2$, $Pb(OCOCH_3)_4$, and $Pb(OCOCH_3)_2 \cdot PbO \cdot 3H_2O$;

organolead compounds such as $Bu_4Pb$, $Ph_4Pb$, $Bu_3PbCl$, $Ph_3PbBr$, $Ph_3Pb$ (or $Ph_6Pb_2$), $Bu_3PbOH$, and $Ph_2PbO$ (wherein Bu represents a butyl group, and Ph represents a phenyl group);

lead alloys such as Pb—Na, Pb—Ca, Pb—Ba, Pb—Sn, and Pb—Sb;

lead minerals such as galena and zinc blende; and hydrates of such lead compounds.

In the case that the compound used dissolves in a starting material of the reaction, the reaction mixture, a reaction by-product or the like, the compound can be used as a homogeneous catalyst, whereas in the case that the compound does not dissolve, the compound can be used as a solid catalyst. Furthermore, it is also preferable to use, as a homogeneous catalyst, a mixture obtained by dissolving a compound as above in a starting material of the reaction, the reaction mixture, a reaction by-product or the like in advance, or by reacting to bring about dissolution.

Furthermore, ion exchangers such as anion exchange resins having tertiary amino groups, ion exchange resins having amide groups, ion exchange resins having at least one type of exchange groups selected from sulfonate groups, carboxylate groups and phosphate groups, and solid strongly basic anion exchangers having quaternary ammonium groups as exchange groups; solid inorganic compounds such as silica, silica-alumina, silica-magnesia, aluminosilicates, gallium silicate, various zeolites, various metal-exchanged zeolites, and ammonium-exchanged zeolites, and so on can also be used as a heterogeneous catalyst.

As a heterogeneous catalyst, a particularly preferably used one is a solid strongly basic anion exchanger having quaternary ammonium groups as exchange groups, examples thereof including a strongly basic anion exchange resin having quaternary ammonium groups as exchange groups, a cellulose strongly basic anion exchanger having quaternary ammonium groups as exchange groups, and an inorganic carrier supported type strongly basic anion exchanger having quaternary ammonium groups as exchange groups. As a strongly basic anion exchange resin having quaternary ammonium groups as exchange groups, for example a styrene type strongly basic anion exchange resin or the like can be preferably used. A styrene type strongly basic anion exchange resin is a strongly basic anion exchange resin having a copolymer of styrene and divinylbenzene as a parent material, and having quaternary ammonium groups (type I or type II) as exchange groups, and can be schematically represented, for example, by the following formula;

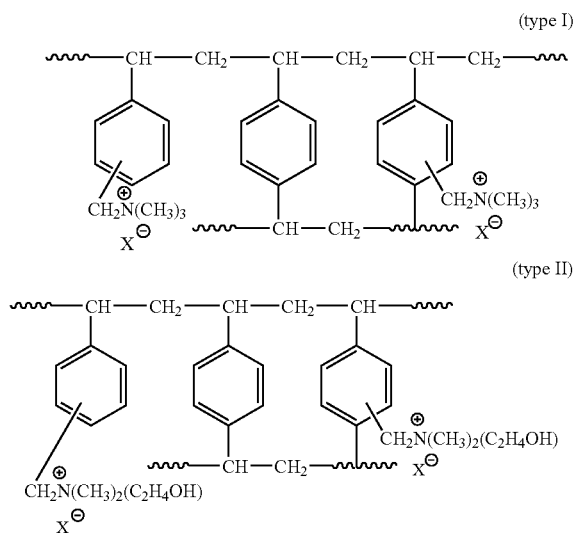

wherein X represents an anion; as X, generally at least one type of anion selected from $F^-$, $Cl^-$, $Br^-$, $I^-$, $HCO_3^-$, $CO_3^{2-}$, $CH_3CO_2^-$, $HCO_2^-$, $IO_3^-$, $BrO_3^-$, and $ClO_3^-$ is used, preferably at least one type of anion selected from $Cl^-$, $Br^-$, $HCO_3^-$, and $CO_3^{2-}$. Moreover, as the structure of the resin parent material, either a gel type one or a macroreticular (MR) type one can be used, the MR type being particularly preferable due to the organic solvent resistance being high.

An example of a cellulose strongly basic anion exchanger having quaternary ammonium groups as exchange groups is cellulose having —$OCH_2CH_2NR_3X$ exchange groups obtained by converting some or all of the —OH groups in the cellulose into trialkylaminoethyl groups. Here, R represents an alkyl group; methyl, ethyl, propyl, butyl or the like is generally used, preferably methyl or ethyl. Moreover, X represents an anion as above.

An inorganic carrier supported type strongly basic anion exchanger having quaternary ammonium groups as exchange groups that can be used in the present invention means an inorganic carrier that has had —$O(CH_2)_nNR_3X$ quaternary ammonium groups introduced thereto by modifying some or all of the —OH surface hydroxyl groups of the inorganic carrier. Here, R and X are as above. n is generally an integer from 1 to 6, preferably n=2. As the inorganic carrier, silica, alumina, silica-alumina, titania, a zeolite, or the like can be used, it being preferable to use silica, alumina, or silica-alumina, particularly preferably silica. Any method can be used as the method of modifying the surface hydroxyl groups of the inorganic carrier.

As the solid strongly basic anion exchanger having quaternary ammonium groups as exchange groups, a commercially available one may be used. In this case, the anion exchanger may also be used as the transesterification catalyst after being subjected to ion exchange with a desired anionic species in advance as pretreatment.

Moreover, a solid catalyst consisting of a macroreticular or gel-type organic polymer having bonded thereto heterocyclic groups each containing at least one nitrogen atom, or an inorganic carrier having bonded thereto heterocyclic groups each containing at least one nitrogen atom can also be preferably used as the transesterification catalyst. Furthermore, a solid catalyst in which some or all of these nitrogen-containing heterocyclic groups have been converted into a quaternary salt can be similarly used. Note that a solid catalyst such as an ion exchanger may also act as a packing in the present invention.

An amount of the catalyst used in the present invention varies depending on the type of the catalyst used, but in the case of continuously feeding in a homogeneous catalyst that dissolves in the reaction liquid under the reaction conditions, the amount used is generally in a range of from 0.0001 to 50% by weight, preferably from 0.005 to 20% by weight, more preferably from 0.01 to 10% by weight, as a proportion of the total weight of the cyclic carbonate and the aliphatic monohydric alcohol fed in as the starting materials. Moreover, in the case of using a solid catalyst installed in the distillation column, the catalyst is preferably used in an amount in a range of from 0.01 to 75 vol %, more preferably from 0.05 to 60 vol %, yet more preferably from 0.1 to 60 vol %, based on the empty column volume of the distillation column.

There are no particular limitations on the method of continuously feeding the cyclic carbonate and the aliphatic monohydric alcohol into the continuous multi-stage distillation column A constituting the reactive distillation column in the present invention; any feeding method may be used so long as the cyclic carbonate and the aliphatic monohydric alcohol can be made to contact the catalyst in a region of at least 5 stages, preferably at least 7 stages, more preferably at least 10 stages, of the distillation column A. That is, the cyclic carbonate and the aliphatic monohydric alcohol can be continuously fed in from a required number of inlets in stages of the continuous multi-stage distillation column A satisfying the conditions described earlier. Moreover, the cyclic carbonate and the aliphatic monohydric alcohol may be introduced into the same stage of the distillation column, or may be introduced into different stages to one another.

The starting materials may be fed continuously into the distillation column A in a liquid form, in a gaseous form, or as a mixture of a liquid and a gas. Other than feeding the starting materials into the distillation column A in this way, it is also preferable to additionally feed in a gaseous starting material intermittently or continuously from the lower portion of the distillation column A. Moreover, another preferable method is one in which the cyclic carbonate is continuously fed in a liquid form or a gas/liquid mixed form into a stage of the distillation column A above the stages in which the catalyst is present, and the aliphatic monohydric alcohol is continuously fed in a gaseous form and/or a liquid form into the lower portion of the distillation column A. In this case, the cyclic carbonate may of course contain the aliphatic monohydric alcohol.

In the present invention, the starting materials fed in may contain the product dialkyl carbonate and/or diol. The content thereof is, for the dialkyl carbonate, generally in a range of from 0 to 40% by weight, preferably from 0 to 30% by weight, more preferably from 0 to 20% by weight, in terms of the percentage by weight of the dialkyl carbonate in the aliphatic monohydric alcohol/dialkyl carbonate mixture, and is, for the diol, generally in a range of from 0 to 10% by weight, preferably from 0 to 7% by weight, more preferably from 0 to 5% by weight, in terms of the percentage by weight of the diol in the cyclic carbonate/diol mixture.

When carrying out the present reaction industrially, besides fresh cyclic carbonate and/or aliphatic monohydric alcohol newly introduced into the reaction system, material having the cyclic carbonate and/or the aliphatic monohydric alcohol as a main component thereof recovered from this process and/or another process can also be preferably used for the starting materials. It is an excellent characteristic feature of the present invention that this is possible. An example of another process is a process in which a diaryl carbonate is produced from the dialkyl carbonate and an aromatic monohydroxy compound, the aliphatic monohydric alcohol being by-produced in this process and recovered. The recovered by-produced aliphatic monohydric alcohol generally often contains the dialkyl carbonate, the aromatic monohydroxy compound, an alkyl aryl ether and so on, and may also contain small amounts of an alkyl aryl carbonate, the diaryl carbonate and so on. The by-produced aliphatic monohydric alcohol may be used as is as a starting material in the present invention, or may be used as a starting material after the amount of contained material having a higher boiling point than that of the aliphatic monohydric alcohol has been reduced through distillation or the like.

A cyclic carbonate preferably used in the present invention is one produced through reaction between, for example, an alkylene oxide such as ethylene oxide, propylene oxide or styrene oxide and carbon dioxide; a cyclic carbonate containing small amounts of such starting material compounds or the like may be used as a starting material in the present invention.

In the present invention, a ratio between the amounts of the cyclic carbonate and the aliphatic monohydric alcohol fed into the reactive distillation column A varies according to the type and amount of the transesterification catalyst and the reaction conditions, but a molar ratio of the aliphatic monohydric alcohol to the cyclic carbonate fed in is generally in a range of from 0.01 to 1000 times. To increase the cyclic carbonate conversion, it is preferable to feed in the aliphatic monohydric alcohol in an excess of at least 2 times the number of mols of the cyclic carbonate. However, if the amount of the aliphatic monohydric alcohol used is too great, then it is necessary to make the apparatus larger. For such reasons, the molar ratio of the aliphatic monohydric alcohol to the cyclic carbonate is preferably in a range of from 2 to 20, more preferably from 3 to 15, yet more preferably from 5 to 12. Furthermore, if much unreacted cyclic carbonate remains, then the unreacted cyclic carbonate may react with the product diol to by-produce oligomers such as a dimer or a trimer, and hence in the case of industrial implementation, it is preferable to reduce the amount of unreacted cyclic carbonate remaining as much as possible. In the process according to the present invention, even if the above molar ratio is not more than 10, the cyclic carbonate conversion can be made to be not less than 98%, preferably not less than 99%, more preferably not less than 99.9%. This is another characteristic feature of the present invention.

In the present invention, preferably not less than approximately 1 ton/hr of a high boiling point reaction mixture $A_B$ containing the diol is continuously produced in the reactive distillation column A, this being fed into a continuous multi-stage distillation column C, and a column bottom component $C_B$ therefrom being subjected to separation by distillation in a continuous multi-stage distillation column E, so as to produce not less than approximately 1 ton/hr of the high-purity diol; the minimum amount of the cyclic carbonate continuously fed into the reactive distillation column A to achieve this is generally 1.55 P ton/hr, preferably 1.5 P ton/hr, more preferably 1.45 P ton/hr, based on the amount P (ton/hr) of the high-purity diol to be produced. In a yet more preferable case, this amount can be made to be less than 1.43 P ton/hr.

There are no particular limitations on the continuous multi-stage distillation column A for carrying out the reactive distillation process in the present invention, but the continuous multi-stage distillation column A is preferably one that enables not only distillation but also reaction to be carried out at the same time so as to be able to produce preferably not less than 1.5 ton/hr of the dialkyl carbonate and/or preferably not less than 1 ton/hr of the diol stably for a prolonged period of time.

In the present invention, a cyclic carbonate and an aliphatic monohydric alcohol are taken as starting materials, the starting materials are continuously fed into a continuous multi-stage distillation column A in which a catalyst is present, reactive distillation is carried out in the column A, a low boiling point reaction mixture $A_T$ containing a produced dialkyl carbonate and the aliphatic monohydric alcohol is continuously withdrawn from an upper portion of the column A in a gaseous form, a high boiling point reaction mixture $A_B$ containing a produced diol is continuously withdrawn from a lower portion of the column A in a liquid form, the high boiling point reaction mixture $A_B$ is continuously fed into a continuous multi-stage distillation column C, material having a lower boiling point than the diol contained in the high boiling point reaction mixture $A_B$ is distilled off as a column top component $C_T$ and/or a side cut component $C_S$ so as to obtain a column bottom component $C_B$, the column bottom component $C_B$ is continuously fed into a continuous multi-stage distillation column E, and the diol is obtained as a side cut component $E_S$ from a side cut outlet of the continuous multi-stage distillation column E, whereby a high-purity diol is produced. The continuous multi-stage distillation column C thus preferably has a function of enabling the material having a lower boiling point than that of the diol contained in the high boiling point reaction mixture $A_B$ to be removed efficiently as the column top component $C_T$ and/or the side cut component $C_S$.

Moreover, for the continuous multi-stage distillation column C, it is preferable for it to be devised such that unreacted cyclic carbonate, which is generally contained in a small amount in the high boiling point reaction mixture $A_B$, is reacted with the diol (e.g. for a temperature and residence time required for this reaction to proceed to completion to be secured). As a result, it can be made to be such that there is substantially no unreacted cyclic carbonate in the column bottom component $C_B$ from the continuous multi-stage distillation column C, which is preferable when carrying out the present invention.

The continuous multi-stage distillation column E used in the present invention must have a function of enabling a high-purity diol to be obtained with a high yield stably for a prolonged period of time from a large amount of the column bottom component $C_B$, and various conditions must be simultaneously satisfied to achieve this.

Specifically, (a) the continuous multi-stage distillation column E comprises a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (9):

$$400 \leq L_1 \leq 3000 \quad (1)$$

$$50 \leq D_1 \leq 700 \quad (2)$$

$$2 \leq L_1/D_1 \leq 50 \quad (3)$$

$$3 \leq n_1 \leq 30 \quad (4)$$

$$600 \leq L_2 \leq 4000 \quad (5)$$

$$100 \leq D_2 \leq 1000 \quad (6)$$

$$2 \leq L_2/D_2 \leq 30 \quad (7)$$

$$5 \leq n_2 \leq 50 \quad (8) \text{ and}$$

$$D_1 \leq D_2 \quad (9);$$

(b) the enrichment section of the continuous multi-stage distillation column E has at least one chimney tray as the internal installed therein, the chimney tray having installed therein at least two chimneys each having an opening having a cross-sectional area S (cm$^2$) satisfying the formula (10):

$$50 \leq S \leq 2000 \quad (10),$$

and each of the chimneys being such that a height h (cm) from the opening of the chimney to a gas outlet of the chimney satisfies the formula (11):

$$20 \leq h \leq 100 \quad (11); \text{ and}$$

(c) a side cut outlet installed for continuously withdrawing the high-purity diol in a liquid form from the continuous multi-stage distillation column E is connected to a liquid collecting section of the chimney tray.

It has been discovered that by subjecting, to separation by distillation in the continuous multi-stage distillation column E having the specified structure simultaneously satisfying the above formulae (1) to (11), the column bottom component $C_B$ obtained by using the continuous multi-stage distillation column C to distill off material having a lower boiling point than that of the diol from a large amount of the high boiling point reaction mixture $A_B$ produced through a reactive distillation process between the cyclic carbonate and the aliphatic monohydric alcohol, a high-purity diol having a purity of preferably not less than 99%, more preferably not less than 99.9%, can be produced on an industrial scale of preferably not less than 1 ton/hr, more preferably not less than 2 ton/hr, stably for a prolonged period of time of, for example, not less than 1000 hours, preferably not less than 3000 hours, more preferably not less than 5000 hours. The reason why it has become possible to produce the high-purity diol on an industrial scale with such excellent effects by implementing the process according to the present invention is not clear, but this is supposed to be due to a composite effect brought about when the conditions of the above formulae (1) to (11) are combined. Note that preferable ranges for the respective factors are described below.

If $L_1$ (cm) is less than 400, then the separation efficiency for the stripping section decreases, and hence the desired separation efficiency cannot be attained. Moreover, to keep down the equipment cost while securing the desired separation efficiency, $L_1$ must be made to be not more than 3000. Furthermore, if $L_1$ is greater than 3000, then the pressure difference between the top and bottom of the column becomes too great, and hence prolonged stable operation becomes difficult, and moreover it becomes necessary to increase the temperature in the lower portion of the column, and hence side reactions become liable to occur. A more preferable range for $L_1$ (cm) is $500 \leq L_1 \leq 2000$, with $600 \leq L_1 \leq 1500$ being yet more preferable.

If $D_1$ (cm) is less than 50, then it is not possible to attain the desired distillation amount. Moreover, to keep down the equipment cost while attaining the desired distillation amount, $D_1$ must be made to be not more than 700. A more preferable range for $D_1$ (cm) is $100 \leq D_1 \leq 600$, with $120 \leq D_1 \leq 500$ being yet more preferable.

If $L_1/D_1$ is less than 2 or greater than 50, then prolonged stable operation becomes difficult. A more preferable range for $L_1/D_1$ is $3 \leq L_1/D_1 \leq 20$, with $4 \leq L_1/D_1 \leq 15$ being yet more preferable.

If $n_1$ is less than 3, then the separation efficiency for the stripping section decreases and hence the desired separation efficiency cannot be attained. Moreover, to keep down the equipment cost while securing the desired separation efficiency, $n_1$ must be made to be not more than 30. Furthermore, if $n_1$ is greater than 30, then the pressure difference between the top and bottom of the column becomes too great, and hence prolonged stable operation becomes difficult, and moreover it becomes necessary to increase the temperature in the lower portion of the column, and hence side reactions become liable to occur. A more preferable range for $n_1$ is $5 \leq n_1 \leq 20$, with $6 \leq n_1 \leq 15$ being yet more preferable.

If $L_2$ (cm) is less than 600, then the separation efficiency for the enrichment section decreases, and hence the desired separation efficiency cannot be attained. Moreover, to keep down the equipment cost while securing the desired separation efficiency, $L_2$ must be made to be not more than 4000. Furthermore, if $L_2$ is greater than 4000, then the pressure difference between the top and bottom of the column becomes too great, and hence prolonged stable operation becomes difficult. Moreover, it becomes necessary to increase the temperature in the lower portion of the column, and hence side reactions become liable to occur. A more preferable range for $L_2$ (cm) is $700 \leq L_2 \leq 3000$, with $800 \leq L_2 \leq 2500$ being yet more preferable.

If $D_2$ (cm) is less than 100, then it is not possible to attain the desired distillation amount. Moreover, to keep down the equipment cost while attaining the desired distillation amount, $D_2$ must be made to be not more than 1000. A more preferable range for $D_2$ (cm) is $120 \leq D_2 \leq 800$, with $150 \leq D_2 \leq 600$ being yet more preferable.

If $L_2/D_2$ is less than 2 or greater than 30, then prolonged stable operation becomes difficult. A more preferable range for $L_2/D_2$ is $3 \leq L_2/D_2 \leq 20$, with $4 \leq L_2/D_2 \leq 15$ being yet more preferable.

If $n_2$ is less than 5, then the separation efficiency for the enrichment section decreases and hence the desired separation efficiency cannot be attained. Moreover, to keep down the equipment cost while securing the desired separation efficiency, $n_2$ must be made to be not more than 50. Furthermore, if $n_2$ is greater than 50, then the pressure difference between the top and bottom of the column becomes too great, and hence prolonged stable operation becomes difficult. Moreover, it becomes necessary to increase the temperature in the lower portion of the column, and hence side reactions become liable to occur. A more preferable range for $n_2$ is $7 \leq n_2 \leq 30$, with $8 \leq n_2 \leq 25$ being yet more preferable. Note that in the present invention, at least one chimney tray must be installed in the enrichment section, and the number of stages therefor is included in $n_2$ above.

Moreover, for the continuous multi-stage distillation column E of the present invention, preferably $D_1 \leq D_2$, more preferably $D_1 < D_2$.

The chimney tray installed in the enrichment section of the continuous multi-stage distillation column E has provided therein at least two chimneys each having an opening having a cross-sectional area S (cm$^2$) in the plane of the tray. Moreover, a chimney cover is preferably installed on an upper opening of each of the chimneys. This chimney cover plays a role in a gaseous component that rises up from lower stages flowing sideways at the upper opening (gas outlet) of the chimney, and moreover plays a role in preventing a liquid component that falls down from upper stages from falling down directly into the lower stages.

The cross-sectional shape of each of the chimneys may be any of triangular, square, polygonal, circular, elliptical, star-shaped or the like, but a square shape or a circular shape is preferably used. Moreover, for each of the chimneys, the cross-sectional shape and area may vary from an upper portion to a lower portion of the chimney, but is preferably constant since then manufacture is simple and inexpensive. Moreover, the at least two chimneys may have different shapes to one another, but preferably have the same shape as one another.

In the present invention, the cross-sectional area S (cm$^2$) of the opening (the part of the chimney having the smallest cross section) of each of the chimneys connected to the chimney tray must satisfy the following formula (10):

$$50 \leq S \leq 2000 \qquad (10).$$

If S is less than 50, then a large number of chimneys are required to attain a predetermined production amount, and hence the equipment cost becomes high. If S is greater than 2000, then the flow of gas in the chimney tray stage is prone to becoming ununiform, and hence prolonged stable operation becomes difficult. A more preferable range for S (cm$^2$) is $100 \leq S \leq 1500$, with $200 \leq S \leq 1000$ being yet more preferable.

Moreover, the height h (cm) from the opening of each of the chimneys to the gas outlet (a lower end of the upper opening of the chimney) of that chimney must satisfy the following formula (II);

$$20 \leq h \leq 100 \qquad (11).$$

The chimney tray used in the present invention generally has installed therein a downcomer portion for allowing the liquid component to fall down into lower stages, and a weir for holding the liquid component. The height of the weir depends on h, but is generally set to approximately 5 to 20 cm less than h. Consequently, if h is less than 20, then the amount of liquid held in the chimney tray becomes low, and hence prolonged stable operation becomes difficult. Moreover, if h is greater than 100, then the amount of liquid held increases, and hence the strength of the equipment must be increased, and thus the equipment cost becomes high, and moreover the residence time of the purified diol in the column increases, which is undesirable. A more preferable range for h (cm) is $30 \leq h \leq 80$, with $40 \leq h \leq 70$ being yet more preferable.

An aperture ratio (a ratio of a total cross-sectional area of the openings in the chimneys to an area of the chimney tray including the total cross-sectional area of the openings) of the chimney tray is preferably in a range of from 5 to 40%. If the aperture ratio is less than 5%, then prolonged stable operation becomes difficult. Moreover, if the aperture ratio is greater than 40%, then the number of chimneys must be increased, or each of the chimneys must be made higher, and in either case the equipment cost becomes high. A more preferable range for the aperture ratio is from 10 to 30%, with from 15 to 25% being yet more preferable.

One of the characteristic features of the present invention is that the at least one chimney tray is installed in the enrichment section (a portion above an inlet for feeding into the column but below the top of the column) of the multi-stage distillation column E, and the high-purity diol is continuously withdrawn in a liquid form from a side cut outlet connected to the bottom of a liquid collecting portion of the chimney tray. The number of chimney trays can be made to be two or more if required, but is generally one. The stage at which the chimney tray is installed may be at any position in the enrichment section, but is preferably a stage that is at least three stages from the bottom of the stages in the enrichment section and at least three stages from the top of the stages in the enrichment section, more preferably a stage that is at least four stages from the bottom of the stages in the enrichment section and at least four stages from the top of the stages in the enrichment section, yet more preferably a stage that is at least five stages from the bottom of the stages in the enrichment section and at least four stages from the top of the stages in the enrichment section.

The continuous multi-stage distillation column E of the present invention is preferably a distillation column having trays and/or packings as an internal in each of the stripping section and the enrichment section. The term "internal" used in the present invention means the part in the distillation column where gas and liquid are actually brought into contact with one another. Examples of the trays include a bubble-cap tray, a sieve tray, a ripple tray, a ballast tray, a valve tray, a counterflow tray, an Unifrax tray, a Superfrac tray, a Maxfrac tray, a dual flow trays, a grid plate tray, a turbogrid plate tray, a Kittel tray, or the like. Examples of the packings include random packings such as a Raschig ring, a Lessing ring, a Pall ring, a Berl saddle, an Intalox saddle, a Dixon packing, a McMahon packing or Heli-Pak, or structured packings such as Mellapak, Gempak, Techno-pack, Flexipac, a Sulzer packing, a Goodroll packing, Glitschgrid or the like. A multi-stage distillation column having both a tray portion and a portion packed with packings can also be used. Furthermore, the term "number of stages $n_1$ or $n_2$ of the internal" used in the present invention means the number of trays in the case of the tray, and the theoretical number of stages in the case of the packing. $n_1$ or $n_2$ in the case of a continuous multi-stage distillation column having both a tray portion and a portion packed with packings is thus the sum of the number of trays and the theoretical number of stages.

In the present invention, it is particularly preferable for the internals in both the stripping section and the enrichment section of the continuous multi-stage distillation column E to be trays. Furthermore, it has been discovered that sieve trays each having a sieve portion and a downcomer portion are particularly good as the tray in terms of the relationship between performance and equipment cost. It has also been discovered that each sieve tray preferably has 150 to 1200 holes/m$^2$ in the sieve portion thereof. A more preferable number of holes is from 200 to 1100 holes/m$^2$, yet more preferably from 250 to 1000 holes/m$^2$. Moreover, it has been discovered that the cross-sectional area per hole of each sieve tray is preferably in a range of from 0.5 to 5 cm$^2$. A more preferable cross-sectional area per hole is from 0.7 to 4 cm$^2$, yet more preferably from 0.9 to 3 cm². Furthermore, it has been discovered that it is particularly preferable if each sieve tray has 150 to 1200 holes/m² in the sieve portion thereof, and the cross-sectional area per hole is in a range of from 0.5 to 5 cm².

An aperture ratio (the ratio of the total cross-sectional area of the holes in one tray stage to the area of the tray) of each of the sieve trays in the stripping section of the continuous multi-stage distillation column E is preferably in a range of from 3 to 25%, more preferably from 3.5 to 22%, yet more preferably from 4 to 20%. Moreover, an aperture ratio (the ratio of the total cross-sectional area of the holes in one tray stage to the area of the tray) of each of the sieve trays in the enrichment section of the continuous multi-stage distillation column E is preferably in a range of from 2 to 20%, more preferably from 3 to 15%, yet more preferably from 3.5 to 13%. Note that in the present invention, the chimney tray installed in the enrichment section is counted in the number of stages, but as described above, the aperture ratio for the chimney tray is different to the aperture ratio for the sieve trays.

It has been shown that by adding the above conditions to the continuous multi-stage distillation column E, the object of the present invention can be attained more easily.

In the present invention, the dialkyl carbonate produced through the reactive distillation in the continuous multi-stage distillation column A is continuously withdrawn from the upper portion of the column in a gaseous form as the low boiling point reaction mixture $A_T$ together with aliphatic monohydric alcohol that has remained unreacted due to generally being used in excess. Moreover, the high boiling point reaction mixture $A_B$ containing the produced diol is continuously withdrawn from the lower portion of the column in a liquid form. The high boiling point reaction mixture $A_B$ having the diol as a main component thereof generally contains 10 to 45% by weight of the residual aliphatic monohydric alcohol, a trace of the dialkyl carbonate, a very small amount (generally not more than 0.2% by weight) of unreacted cyclic carbonate, a small amount (generally not more than 0.4% by weight) of by-products having a lower boiling point than the diol (a 2-alkoxyethanol etc.), and a small amount (generally not more than 0.4% by weight) of by-products having a higher boiling point than that of the diol (e.g. a dialkylene glycol) including catalyst.

Material having a lower boiling point than that of the diol (the aliphatic monohydric alcohol, a trace of the dialkyl carbonate and by-produced $CO_2$, low boiling point by-products) and a small amount of the diol in the high boiling point reaction mixture $A_B$ continuously fed into the continuous multi-stage distillation column C are thus continuously withdrawn as the column top component $C_T$ and/or the side cut component $C_S$, while the diol containing the catalyst and a small amount of high boiling point by-products is continuously withdrawn as the column bottom component $C_B$. In the present invention, the concentration of the diol in the column bottom component $C_B$ is generally not less than 95% by weight, preferably not less than 97% by weight, more preferably not less than 98% by weight.

Moreover, in the process of the present invention, a very small amount (generally not more than 0.2% by weight) of unreacted cyclic carbonate fed into the continuous multi-stage distillation column C can be reacted with the diol, which is present in a large amount in the continuous multi-stage distillation column C, to produce a dialkylene glycol, and hence it is easy to make the amount of unreacted cyclic carbonate present substantially zero; in the present invention, the column bottom component $C_B$ continuously fed into the continuous multi-stage distillation column E thus generally has substantially no unreacted cyclic carbonate therein.

Note that, generally, with an objective of obtaining an ultra-high-purity diol having a further reduced content of an aldehyde which may be contained in the diol in trace amount, or an ultra-high-purity diol having a high UV transmissivity, it is also preferable to feed a small amount of water into the lower portion of the continuous multi-stage distillation column E in accordance with the process described in Patent Document 9 (Japanese Patent Application Laid-Open No. 2002-308804) or Patent Document 10 (Japanese Patent Application Laid-Open No. 2004-131394).

The distillation conditions for the continuous multi-stage distillation column E used in the present invention vary depending on the form of the internal in the distillation column and the number of stages, the type, composition and amount of the column bottom component $C_B$ of the distillation column C fed in, the purity of the diol required, and so on. The column bottom temperature is generally preferably a specified temperature in a range of from 110 to 210° C. A more preferable column bottom temperature range is from 120 to 190° C., yet more preferably from 130 to 170° C. The column bottom pressure varies depending on the composition in the column and the column bottom temperature used, but is generally in a range of from 8000 to 40000 Pa, preferably 10000 to 33000 Pa, more preferably 1.2000 to 27000 Pa.

Moreover, the reflux ratio for the continuous multi-stage distillation column E is preferably in a range of from 6 to 50, more preferably from 8 to 45, yet more preferably from 10 to 30.

In the present invention, a column top component $E_T$ from the continuous multi-stage distillation column E comprises a small amount of the diol (generally not more than 10% by weight of the diol fed in); moreover, in the case that water is fed into the continuous multi-stage distillation column E, almost all of the water fed in is withdrawn in the column top component $E_T$. The column top component $E_T$ is generally recycled into the continuous multi-stage distillation column C, and then fed back into the continuous multi-stage distillation column E as some of the column bottom component $C_B$, and thus recovered as high-purity diol. Moreover, a column bottom component $E_B$ from the continuous multi-stage distillation column E contains high boiling point by-products and catalyst component containing a small amount of the diol. The side cut component $E_S$ from the continuous multi-stage distillation column E generally contains not less than 99%, preferably not less than 99.9%, more preferably not less than 99.99%, of the high-purity diol. That is, in the present invention, the content in the side cut component $E_S$ of impurities (a dialkylene glycol etc.) having a higher boiling point than that of the diol can generally easily be made to be not more than 1% by weight, preferably not more than 0.1% by weight, more preferably not more than 0.01% by weight. Moreover, in a preferable embodiment of the present invention, the reaction is carried out using starting materials and a catalyst not containing a halogen, and hence the produced diol can be made to not contain a halogen at all. In the present invention, a diol having a halogen content of not more than 0.1 ppm, preferably not more than 1 ppb, can thus be easily produced.

That is, in the present invention, a high-purity diol having a content of impurities having a higher boiling point than that of the diol such as a dialkylene glycol of not more than 200 ppm, and a halogen content of not more 0.1 ppm can be easily produced, preferably a high-purity diol having a content of impurities having a higher boiling point than that of the diol such as a dialkylene glycol of not more than 100 ppm, and a halogen content of not more 1 ppb can be easily produced.

In the present invention, the reaction yield and the purification yield are thus high, and hence the high-purity diol can be produced with a high yield of generally not less than 97%, preferably not less than 98%, more preferably not less than 99%, based on the cyclic carbonate used.

The material constituting each of the continuous multi-stage distillation columns A, C and E used in the present invention is generally a metallic material such as carbon steel or stainless steel. In terms of the quality of the dialkyl carbonate and diol to be produced, stainless steel is preferable.

EXAMPLES

Although the following is a more detailed description of the present invention through examples, the present invention is not limited to the following examples. Note that the halogen content was measured using ion chromatography.

Example 1

A continuous multi-stage distillation column E as shown in FIG. 1 having $L_1$=850 cm, $D_1$=160 cm, $L_1/D_1$=5.3, $n_1$=8, $L_2$=1000 cm, $D_2$=200 cm, $L_2/D_2$=5, and $n_2$=11, and having one chimney tray stage installed at the $5^{th}$ stage from the top of the enrichment section stages was used. In this example, sieve trays (cross-sectional area per hole=approximately 1.3 cm$^2$) were used in both the stripping section and the enrichment section as the internal excluding the chimney tray. In the stripping section, the number of holes in each of the sieve trays was approximately 300 to 370/m$^2$, and the aperture ratio was in a range of from 4 to 5%. Moreover, in the enrichment section, the number of holes in each of the sieve trays was approximately 300 to 450/m$^2$, and the aperture ratio was in a range of from 3 to 4%. The chimney tray had twelve chimneys therein, each of the chimneys having S=approximately 500 cm$^2$ and h=55 cm, and the aperture ratio being in a range of from 15 to 20%. The chimney tray had a downcomer portion, the weir height being 40 cm.

A starting material containing ethylene carbonate (EC) and methanol (MeOH) (molar ratio MeOH/EC=8.4) and a catalyst (KOH in ethylene glycol subjected to thermal dehydration treatment; K concentration 0.1% by weight based on EC) was continuously fed into a continuous multi-stage distillation column A, and reactive distillation was carried out, whereby 3.205 ton/hr of a column bottom component $A_B$ was continuously withdrawn. The ethylene carbonate conversion was 100%, and the ethylene glycol selectivity was 99.8%. The column bottom component $A_B$, which contained 0.99 ton/hr of methanol, 0.001 ton 1 hr of dimethyl carbonate, 0.009 ton/hr of 2-methoxyethanol, 2.186 ton/hr of ethylene glycol, and 0.019 ton/hr of diethylene glycol and catalyst component, was continuously fed into a continuous multi-stage distillation column C from an inlet. This inlet was installed between the trays in the $9^{th}$ and $10^{th}$ stages from the bottom of the continuous multi-stage distillation column C. Separate to this, 0.155 ton/hr of a column top component $E_T$ (0.137 ton/hr of ethylene glycol, 0.019 ton/hr of water) from the continuous multi-stage distillation column E was continuously fed into the continuous multi-stage distillation column C via a reboiler at the bottom of the continuous multi-stage distillation column C.

A column top component $C_T$ containing 0.968 ton/hr of methanol, 0.001 ton/hr of dimethyl carbonate, and 0.019 ton/hr of water, a side cut component $C_S$ containing 0.022 ton/hr of methanol, 0.0093 ton/hr of 2-methoxyethanol, and 0.003 ton/hr of ethylene glycol, and a column bottom component $C_B$ containing 2.32 ton/hr of ethylene glycol, and 0.019 ton/hr of diethylene glycol, catalyst component and high boiling point by-products were continuously withdrawn from the continuous multi-stage distillation column C.

2.339 Ton/hr of the column bottom component $C_B$ was continuously fed into the continuous multi-stage distillation column E from an inlet 1 installed between the $8^{th}$ and $9^{th}$ stages from the bottom of the column. 0.019 Ton/hr of water having an oxygen concentration of not more than 10 ppm was fed into the continuous multi-stage distillation column E via a reboiler 7 from an inlet 5 in the bottom of the column. The continuous multi-stage distillation column E was operated continuously with a column bottom temperature of approximately 149° C., a column bottom pressure of approximately 14600 Pa, and a reflux ratio of 11.

It was possible to attain stable steady state operation after 24 hours. A column top component $E_T$ continuously withdrawn from the top 2 of the continuous multi-stage distillation column E at 0.155 ton/hr contained 0.136 ton/hr of ethylene glycol and 0.019 ton/hr of water. This column top component $E_T$ was recycled back into the continuous multi-stage distillation column C. A column bottom component $E_B$ continuously withdrawn from the bottom 3 of the continuous multi-stage distillation column E at 0.04 ton/hr contained 0.02 ton/hr of ethylene glycol, and 0.02 ton/hr of diethylene glycol, catalyst component and high boiling point by-products. The purity of ethylene glycol in a side cut component $E_S$ continuously withdrawn at 2.164 ton/hr from a side cut 4 of the continuous multi-stage distillation column E was not less than 99.99%, the content of high boiling point impurities such as diethylene glycol being not more than 10 ppm, and the halogen content being outside the detection limit, i.e. not more than 1 ppb.

The high-purity ethylene glycol yield based on the ethylene carbonate was 98.6%.

Prolonged continuous operation was carried out under these conditions. After 500 hours, 2000 hours, 4000 hours, 5000 hours, and 6000 hours, the produced amounts of ethylene glycol per hour were 2.162 ton, 2.162 ton, 2.162 ton, 2.162 ton, and 2.162 ton, and hence operation was very stable. The purity of the ethylene glycol was not less than 99.99% in each case, and the halogen content was outside the detection limit, i.e. not more than 1 ppb. Moreover, the aldehyde content measured using the method of Patent Document 15 (Japanese Patent Application Laid-Open No. 2003-342209) was not more than 0.2 ppm, and the UV transmissivity at 220 nm was 90%.

Example 2

High-purity ethylene glycol was produced using the same continuous multi-stage distillation column E as in Example 1 and a similar process.

2.472 Ton/hr of the column bottom component $C_B$ continuously withdrawn from the continuous multi-stage distillation column C (2.439 Ton/hr of ethylene glycol, and 0.033 ton/hr of diethylene glycol, catalyst component and high boiling point by-products) was continuously fed into the continuous multi-stage distillation column E from the inlet 1.

0.022 Ton/hr of water having an oxygen concentration of not more than 10 ppm was fed into the continuous multi-stage distillation column E via the reboiler 7 from the inlet 5 in the bottom of the column. The continuous multi-stage distillation column E was operated continuously with a column bottom temperature of approximately 162° C., a column bottom pressure of approximately 17300 Pa, and a reflux ratio of 12.

It was possible to attain stable steady state operation after 24 hours. The column top component $E_T$ continuously withdrawn from the top 2 of the continuous multi-stage distillation column E at 0.192 ton/hr contained 0.17 ton/hr of ethylene glycol and 0.022 ton/hr of water. This column top component $E_T$ was recycled back into the continuous multi-stage distillation column C. The column bottom component $E_B$ continuously withdrawn from the bottom 3 of the continuous multi-stage distillation column E at 0.055 ton/hr contained 0.015 ton/hr of ethylene glycol, and 0.04 ton/hr of diethylene glycol, catalyst component and high boiling point by-products. The purity of ethylene glycol in the side cut component $E_S$ continuously withdrawn at 2.29 ton/hr from the side cut 4 of the continuous multi-stage distillation column E was not less than 99.99%, the content of high boiling point impurities such as diethylene glycol being not more than 10 ppm, and the halogen content being outside the detection limit, i.e. not more than 1 ppb.

The high-purity ethylene glycol yield based on the ethylene carbonate was 98.5%.

Prolonged continuous operation was carried out under these conditions. After 1000 hours, 2000 hours, 3000 hours, and 5000 hours, the produced amounts of ethylene glycol per hour were 2.29 ton, 2.29 ton, 2.29 ton, and 2.29 ton, and hence operation was very stable. The purity of the ethylene glycol was not less than 99.99% in each case, and the halogen content was outside the detection limit, i.e. not more than 1 ppb. Moreover, the aldehyde content was not more than 0.2 ppm, and the UV transmissivity at 220 nm was 90%.

Example 3

A continuous multi-stage distillation column E very similar to that used in Example 1 was used. However, in the enrichment section, the number of holes in each of the sieve trays was approximately 400 to 450/m$^2$, and the aperture ratio was in a range of from 5 to 6%.

2.925 Ton/hr of the column bottom component $C_B$ continuously withdrawn from the continuous multi-stage distillation column C (2.877 ton 1 hr of ethylene glycol, and 0.048 ton/hr of diethylene glycol, catalyst component and high boiling point by-products) was continuously fed into the continuous multi-stage distillation column E from the inlet 1.

0.026 Ton/hr of water having an oxygen concentration of not more than 10 ppm was fed into the continuous multi-stage distillation column E via the reboiler 7 from the inlet 5 in the bottom of the column. The continuous multi-stage distillation column E was operated continuously with a column bottom temperature of approximately 155° C., a column bottom pressure of approximately 18000 Pa, and a reflux ratio of 10.

It was possible to attain stable steady state operation after 24 hours. The column top component $E_T$ continuously withdrawn from the top 2 of the continuous multi-stage distillation column E at 0.233 ton/hr contained 0.207 ton/hr of ethylene glycol and 0.026 ton/hr of water. This column top component $E_T$ was recycled back into the continuous multi-stage distillation column C. The column bottom component $E_B$ continuously withdrawn from the bottom 3 of the continuous multi-stage distillation column E at 0.07 ton/hr contained 0.02 ton/hr of ethylene glycol, and 0.05 ton/hr of diethylene glycol, catalyst component and high boiling point by-products. The purity of ethylene glycol in the side cut component $E_S$ continuously withdrawn at 2.648 ton/hr from the side cut 4 of the continuous multi-stage distillation column E was not less than 99.99%, the content of high boiling point impurities such as diethylene glycol being not more than 10 ppm, and the halogen content being outside the detection limit, i.e. not more than 1 ppb.

The high-purity ethylene glycol yield based on the ethylene carbonate was 98.7%.

Prolonged continuous operation was carried out under these conditions. After 1000 hours, 2000 hours, and 3000 hours, the produced amounts of ethylene glycol per hour were 2.648 ton, 2.648 ton, and 2.648 ton, and hence operation was very stable. The purity of the ethylene glycol was not less than 99.99% in each case, and the halogen content was outside the detection limit, i.e. not more than 1 ppb. Moreover, the aldehyde content was not more than 0.2 ppm, and the UV transmissivity at 220 nm was 90%.

Example 4

A continuous multi-stage distillation column E very similar to that used in Example 1 was used. However, in the stripping section, the number of holes in each of the sieve trays was approximately 650 to 750/m$^2$, and the aperture ratio was in a range of from 8 to 10%, and in the enrichment section, the number of holes in each of the sieve trays was approximately 500 to 650/m$^2$, and the aperture ratio was in a range of from 6 to 8%.

5.852 Ton/hr of the column bottom component $C_B$ continuously withdrawn from the continuous multi-stage distillation column C (5.754 ton 1 hr of ethylene glycol, and 0.098 ton/hr of diethylene glycol, catalyst component and high boiling point by-products) was continuously fed into the continuous multi-stage distillation column E from the inlet 1.

0.05 Ton/hr of water having an oxygen concentration of not more than 10 ppm was fed into the continuous multi-stage distillation column E via the reboiler 7 from the inlet 5 in the bottom of the column. The continuous multi-stage distillation column E was operated continuously with a column bottom temperature of approximately 160° C., a column bottom pressure of approximately 21300 Pa, and a reflux ratio of 13.

It was possible to attain stable steady state operation after 24 hours. The column top component $E_T$ continuously withdrawn from the top 2 of the continuous multi-stage distillation column E at 0.45 ton/hr contained 0.4 ton/hr of ethylene glycol and 0.05 ton/hr of water. This column top component $E_T$ was recycled back into the continuous multi-stage distillation column C. The column bottom component $E_B$ continuously withdrawn from the bottom 3 of the continuous multi-stage distillation column E at 0.2 ton/hr contained 0.1 ton/hr of ethylene glycol, and 0.1 ton/hr of diethylene glycol, catalyst component and high boiling point by-products. The purity of ethylene glycol in the side cut component $E_S$ continuously withdrawn at 5.202 ton/hr from the side cut 4 of the continuous multi-stage distillation column E was not less than 99.99%, the content of high boiling point impurities such as diethylene glycol being not more than 10 ppm, and the halogen content being outside the detection limit, i.e. not more than 1 ppb.

The high-purity ethylene glycol yield based on the ethylene carbonate was 97.6%.

Prolonged continuous operation was carried out under these conditions. After 500 hours, 1000 hours, and 1500 hours, the produced amounts of ethylene glycol per hour were 5.202 ton, 5.202 ton, and 5.202 ton, and hence operation was very stable. The purity of the ethylene glycol was not less than 99.99% in each case, and the halogen content was outside the detection limit, i.e. not more than 1 ppb. Moreover, the aldehyde content was not more than 0.2 ppm, and the UV transmissivity at 220 nm was 90%.

INDUSTRIAL APPLICABILITY

According to the present invention, it has been discovered that, from out of a dialkyl carbonate and a diol produced through a reactive distillation system from a cyclic carbonate and an aliphatic monohydric alcohol, a high-purity diol having a purity of not less than 97%, preferably not less than 99%, more preferably not less than 99.9%, a content of high boiling point impurities including a dialkylene glycol of preferably not more than 200 ppm, more preferably not more than 100 ppm, yet more preferably not more than 10 ppm, and a halogen content of preferably not more than 0.1 ppm, more preferably not more than 1 ppb, can be obtained on an industrial scale of not less than 1 ton/hr, preferably not less than 2 ton/hr, more preferably not less than 3 ton/hr, with a high yield stably for a prolonged period of time of not less than 1000 hours, preferably not less than 3000 hours, more preferably not less than 5000 hours. This high-purity diol (e.g. high-purity ethylene glycol) has a higher purity than such a diol industrially produced using an existing production process (e.g. an ethylene oxide hydration process), and hence is useful as a starting material for a high-quality polyester (e.g. PET fiber or PET resin).

We claim:

1. An industrial process for the production of a high-purity diol in which a high-purity diol is produced by taking a cyclic carbonate and an aliphatic monohydric alcohol as starting materials, continuously feeding the starting materials into a continuous multi-stage distillation column A in which a catalyst is present, carrying out reactive distillation in said column A, continuously withdrawing a low boiling point reaction mixture $A_T$ containing a produced dialkyl carbonate and the aliphatic monohydric alcohol from an upper portion of the column A in a gaseous form, continuously withdrawing a high boiling point reaction mixture $A_B$ containing a produced diol from a lower portion of the column A in a liquid form, continuously feeding said high boiling point reaction mixture $A_B$ into a continuous multi-stage distillation column C, distilling off material having a lower boiling point than the diol contained in said high boiling point reaction mixture $A_B$ as a column top component $C_T$ and/or a side cut component $C_S$ so as to obtain a column bottom component $C_B$, continuously feeding the column bottom component $C_B$ into a continuous multi-stage distillation column E, and obtaining the diol as a side cut component $E_S$ from a side cut outlet of the continuous multi-stage distillation column E, wherein:

(a) said continuous multi-stage distillation column E comprises a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (9):

$$400 \leq L_1 \leq 3000 \tag{1}$$

$$50 \leq D_1 \leq 700 \tag{2}$$

$$2 \leq L_1/D_1 \leq 50 \tag{3}$$

$$3 \leq n_1 \leq 30 \tag{4}$$

$$600 \leq L_2 \leq 4000 \tag{5}$$

$$100 \leq D_2 \leq 1000 \tag{6}$$

$$2 \leq L_2/D_2 \leq 30 \tag{7}$$

$$5 \leq n_2 \leq 50 \tag{8) and}$$

$$D_1 \leq D_2 \tag{9};$$

(b) the enrichment section of said continuous multi-stage distillation column E has at least one chimney tray as an internal installed therein, said chimney tray having installed therein at least two chimneys each having an opening having a cross-sectional area S (cm²) satisfying the formula (10):

$$50 \leq S \leq 2000 \tag{10},$$

and each of the chimneys being such that a height h (cm) from the opening of the chimney to a gas outlet of the chimney satisfies the formula (11):

$$20 \leq h \leq 100 \tag{11}; and$$

(c) the diol is continuously withdrawn in a liquid form from the side cut outlet, which is connected to a liquid collecting section of said chimney tray of said continuous multi-stage distillation column E.

2. The process according to claim 1, wherein a produced amount of the high-purity diol is not less than 1 ton/hr.

3. The process according to claim 1 or 2, wherein $L_1$, $D_1$, $L_1/D_1$, $n_1$, $L_2$, $D_2$, $L_2/D_2$, and $n_2$ for said continuous multi-stage distillation column E satisfy $500 \leq L_1 \leq 2000$, $100 \leq D_1 \leq 500$, $3 \leq L_1/D_1 \leq 20$, $5 \leq n_1 \leq 20$, $700 \leq L_2 \leq 3000$, $120 \leq D_2 \leq 800$, $3 \leq L_2/D_2 \leq 20$, $7 \leq n_2 \leq 30$, and $D_1 < D_2$.

4. The process according to claim 1, wherein an internal excluding the chimney tray in each of the stripping section and the enrichment section of said continuous multi-stage distillation column E is a tray and/or a packing.

5. The process according to claim 4, wherein the internal excluding the chimney tray in each of the stripping section and the enrichment section of said continuous multi-stage distillation column E is the tray.

6. The process according to claim 5, wherein said tray is a sieve tray.

7. The process according to claim 6, wherein said sieve tray has 150 to 1200 holes/m² in a sieve portion thereof, and a cross-sectional area per hole in a range of from 0.5 to 5 cm².

8. The process according to claim 6, wherein said sieve tray has 200 to 1100 holes/m² in a sieve portion thereof, and a cross-sectional area per hole in a range of from 0.7 to 4 cm².

9. The process according to claim 6, wherein said sieve tray has 250 to 1000 holes/m² in a sieve portion thereof, and a cross-sectional area per hole in a range of from 0.9 to 3 cm².

10. The process according to claim 6, wherein an aperture ratio (a ratio of a total cross-sectional area of the hole in one tray stage to an area of the tray) of said sieve tray in the stripping section of said continuous multi-stage distillation column E is in a range of from 3 to 25%.

11. The process according to claim 6, wherein an aperture ratio (a ratio of a total cross-sectional area of the hole in one tray stage to an area of the tray) of said sieve trays in the enrichment of said continuous multi-stage distillation column E is in a range of from 2 to 20%.

12. The process according to claim 1, wherein an aperture ratio (a ratio of a total cross-sectional area of the opening in the chimney to an area of the chimney tray including the total cross-sectional area of the opening) of the chimney tray is in a range of from 5 to 40%.

13. The process according to claim 1, wherein a column bottom temperature of said continuous multi-stage distillation column E is in a range of from 110 to 210° C.

14. The process according to claim 1, wherein a reflux ratio of said continuous multi-stage distillation column E is in a range of from 6 to 100.

15. The process according to claim 1, wherein a purity of the diol in said side cut component $E_S$ is not less than 99%.

16. The process according to claim 1, wherein a purity of the diol in said side cut component $E_S$ is not less than 99.9%.

17. The process according to claim 1, wherein the high-purity diol produced comprises a content of high boiling point impurities such as a dialkylene glycol of not more than 200 ppm, and a halogen content of not more than 0.1 ppm.

18. The process according to claim 1, wherein the high-purity diol produced comprises a content of high boiling point impurities such as a dialkylene glycol of not more than 100 ppm, and a halogen content of not more than 1 ppb.

19. A continuous multi-stage distillation column being a continuous multi-stage distillation column E for producing a high-purity diol, wherein:

(a) said continuous multi-stage distillation column E comprises a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (9):

$$400 \leq L_1 \leq 3000 \tag{1}$$

$$50 \leq D_1 \leq 700 \tag{2}$$

$$2 \leq L_1/D_1 \leq 50 \tag{3}$$

$$3 \leq n_1 \leq 30 \tag{4}$$

$$600 \leq L_2 \leq 4000 \tag{5}$$

$$100 \leq D_2 \leq 1000 \tag{6}$$

$$2 \leq L_2/D_2 \leq 30 \tag{7}$$

$$5 \leq n_2 \leq 50 \tag{8} \text{ and}$$

$$D_1 \leq D_2 \tag{9};$$

(b) the enrichment section of said continuous multi-stage distillation column E has at least one chimney tray as an internal installed therein, said chimney tray having installed therein at least two chimneys each having an opening having a cross-sectional area S (cm$^2$) satisfying the formula (10):

$$50 \leq S \leq 2000 \tag{10},$$

and each of the chimneys being such that a height h (cm) from the opening of the chimney to a gas outlet of the chimney satisfies the formula (11):

$$20 \leq h \leq 100 \tag{11}; \text{ and}$$

(c) said multi-stage distillation column E comprises a side cut outlet installed for continuously withdrawing the high-purity diol in a liquid form from said continuous multi-stage distillation column E is connected to a liquid collecting section of said chimney tray.

20. The continuous multi-stage distillation column according to claim 19, wherein $L_1$, $D_1$, $L_1/D_1$, $n_1$, $L_2$, $D_2$, $L_2/D_2$, and $n_2$ satisfy $500 \leq L_1 \leq 2000$, $100 \leq D_1 \leq 500$, $3 \leq L_1/D_1 \leq 20$, $5 \leq n_1 \leq 20$, $700 \leq L_2 \leq 3000$, $120 \leq D_2 \leq 800$, $3 \leq L_2/D_2 \leq 20$, $7 \leq n_2 \leq 30$, and $D_1 < D_2$.

21. The continuous multi-stage distillation column according to claim 19 or 20, wherein an internal excluding the chimney tray in each of the stripping section and the enrichment section is a tray and/or a packing.

22. The continuous multi-stage distillation column according to claim 21, wherein the internal excluding the chimney tray in each of the stripping section and the enrichment section is the tray.

23. The continuous multi-stage distillation column according to claim 22, wherein said tray is a sieve tray.

24. The continuous multi-stage distillation column according to claim 23, wherein said sieve trays has 150 to 1200 holes/m$^2$ in a sieve portion thereof, and a cross-sectional area per hole in a range of from 0.5 to 5 cm$^2$.

25. The continuous multi-stage distillation column according to claim 23, wherein said sieve trays has 200 to 1100 holes/m$^2$ in a sieve portion thereof, and a cross-sectional area per hole in a range of from 0.7 to 4 cm$^2$.

26. The continuous multi-stage distillation column according to claim 23, wherein said sieve trays has 250 to 1000 holes/m$^2$ in a sieve portion thereof, and a cross-sectional area per hole in a range of from 0.9 to 3 cm$^2$.

27. The continuous multi-stage distillation column according to claim 23, wherein an aperture ratio (a ratio of a total cross-sectional area of the hole in one tray stage to an area of the tray) of said sieve tray in the stripping section is in a range of from 3 to 25%.

28. The continuous multi-stage distillation column according to claim 23, wherein an aperture ratio (a ratio of a total cross-sectional area of the hole in one tray stage to an area of the tray) of said sieve tray in the enrichment section is in a range of from 2 to 20%.

29. The continuous multi-stage distillation column according to claim 23, wherein an aperture ratio (a ratio of a total cross-sectional area of the opening in the chimney to an area of the chimney tray including the total cross-sectional area of the opening) of the chimney tray is in a range of from 5 to 40%.

* * * * *